United States Patent [19]
Friedman

[11] Patent Number: 5,371,826
[45] Date of Patent: Dec. 6, 1994

[54] DENTAL FIBER OPTIC LIGHT BUNDLE WITH UNIFORM TAPER

[75] Inventor: Joshua Friedman, Danbury, Conn.

[73] Assignee: Demetron Research Corp., Danbury, Conn.

[21] Appl. No.: 112,102

[22] Filed: Aug. 27, 1993

[51] Int. Cl.⁵ .............................................. G02B 6/26
[52] U.S. Cl. .................................................... 385/115
[58] Field of Search ................ 385/115, 116, 119, 120

[56] References Cited

U.S. PATENT DOCUMENTS

| | | | |
|---|---|---|---|
| 2,945,958 | 7/1960 | Morris | 250/230 |
| 4,076,378 | 2/1978 | Cole | 385/115 |
| 4,332,439 | 6/1982 | Lübbers et al. | 385/115 X |
| 4,688,884 | 8/1987 | Scifres et al. | 385/43 X |
| 4,697,867 | 10/1987 | Blanc et al. | 385/43 |
| 4,723,825 | 2/1988 | Herold | 385/43 X |
| 4,792,692 | 12/1988 | Herold et al. | 250/504 H |
| 4,836,782 | 6/1989 | Gonser | 433/229 |

Primary Examiner—Akm E. Ullah
Attorney, Agent, or Firm—E. Lieberstein

[57] ABSTRACT

A fiber optic light guide for forming a concentrated high intensity light, comprising a multiplicity of fiber optic strands bundled together, with each strand uniformly tapered to form an elongated tapered section having a cumulative taper of less than five degrees (<5°) and a curved section extending distally from said elongated tapered section.

8 Claims, 3 Drawing Sheets

5,371,826

1

DENTAL FIBER OPTIC LIGHT BUNDLE WITH UNIFORM TAPER

FIELD OF THE INVENTION

This invention relates to a fiber optic light guide and light-curing unit for producing a convergent beam of concentrated high-intensity light for curing a photocurable dental composition.

BACKGROUND OF THE INVENTION

Photocurable materials are commonly used in dentistry as sealants, adhesives, and as filler material for filling dental cavities. To cure the photocurable material, it is exposed to radiant energy in a preselected spectral range, typically in either the long-wave ultraviolet or blue visible spectrum, tailored to the composition of the photocurable material. A light-curing unit containing a reflector lamp is used to irradiate the photocurable material by directing light from the reflector lamp through a light guide positioned with its distal end adjacent to the photocurable material to be cured. The light guide functions to channel the light to the material at the site of the dental restoration.

The physics of the transmission of light through a light conductor is well known, and is not unique to the field of dentistry. Any conventional text on optics will provide the fundamentals to compute the critical angle and the numerical aperture for maximum transmission of light through a conductive medium of known geometry, composition, and refractive index. It is the result of practical factors, such as limited accessibility, maneuverability, and size, that complicates the design of a dental light guide and light-curing unit. For example, to provide maximum accessibility and maneuverability within the oral cavity of a patient, the dental practitioner requires the light guide to have a curved end section. Substantial emphasis has been given to the design of a light guide to maximize the transmission of light from a reflector lamp of given dimensions operating at a given voltage rating under the constraints imposed by the dental practitioner and practical considerations of length and diameter.

The conventional light guide is a solid conductor of either glass or plastic, or is composed of a fiber optic conductor consisting of multiple strands of glass fiber held together as a flexible bundle or fused into a solid rod of individual fibers.

SUMMARY OF THE INVENTION

The light guide of the present invention is a fiber optic conductor having an elongated, conical, tapered section and a tapered curved section which generates a convergent beam of high-intensity light at the distal end of the curved section, with minimal loss of light through the light guide.

The light guide of the present invention comprises: a multiplicity of fiber optic strands bundled together to form a solid conductor of fixed geometry, having an elongated, conical-shaped section over a substantial portion of its length, and a curved section extending distally from the conical section, wherein each fiber optic strand is composed of a tapered core having a predetermined refractive index, and a cladded coating having a refractive index lower than the refractive index of said core, with each fiber optic strand having a complementary tapered geometry, with a taper angle substan-

2 tially equivalent to the taper angle of each other fiber optic strand, such that the cumulative taper of all of said fiber optic strands form an optical taper for said rod, having a taper angle proportional to the number of tapered strands in said bundle multiplied by the taper angle of said fiber optic strands.

BRIEF DESCRIPTION OF THE DRAWINGS

Other objects and advantages Of the present invention will become apparent from the following detailed description when read in conjunction with the accompanying drawings of which:

FIG. 4B is an enlarged cross-section of a fiber optic strand showing the taper angle ("T");

FIG. 4A is an enlarged section of a single fiber optic strand of FIG. 4;

DETAILED DESCRIPTION OF THE INVENTION

Figure 1:
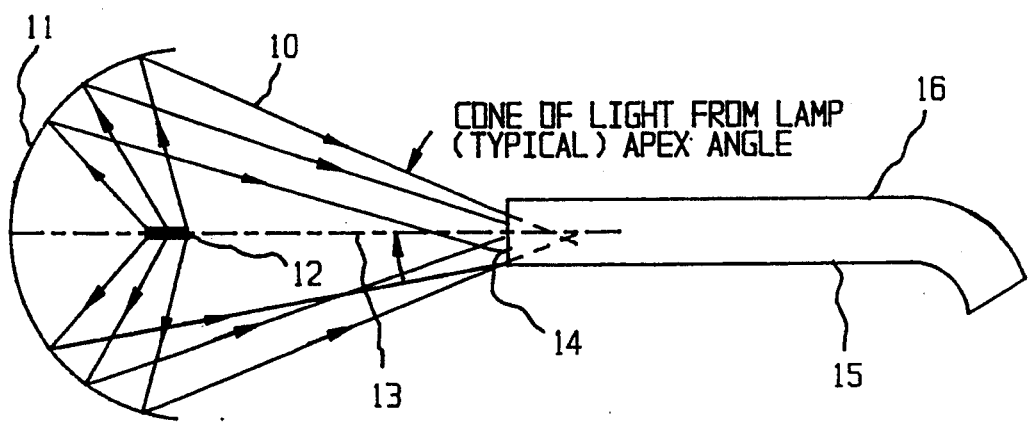
FIG. 1 is a schematic of the light-curing unit of the present invention, including a lamp assembly and a light guide.

The source of light (10), shown schematically in FIG. 1, comprises: a lamp filament (12) and a parabolic reflector (11). The lamp filament (12) is disposed on the optic axis (13) within the light source (10) to reflect cones of light off the reflector (11) toward a focal spot where a light guide (15) is positioned. The light guide (15) has a light-receiving surface (14) oriented perpendicular to the optic axis (13) to receive the incident cones of light. The cones of light are received at an acceptance angle, which for maximum efficiency, should be as large as possible. The mathematical sine of the maximum acceptance angle, known as the numerical aperture, is determined by the optical properties of the fiber optic material and its shape. The diameter of the light guide (15) at the light-receiving surface (14) is selected to maximize the efficient collection of light incident at the focal plane, coinciding with the light-receiving surface (14), and is generally in a range of between 8-13 min. It is conventional for the light guide (15) to have a curved end section (16) to satisfy the requirements of maneuverability and accessibility of the light guide (15) for placement in the oral cavity of a dental patient. The curved section (16) has a radius of curvature which is chosen in proportion to the diameter of the curved end of the light guide (15), with an angle of curvature of from thirty degrees (30°) to sixty degrees (60°), for a diameter range of between 0.3 and 0.6 inches.

It is known that if a light guide is tapered, the taper will reduce the angle of incidence for each reflection and cause a concentration of the light rays at the distal end of the light guide. This is true for any light conducting medium, and will apply to a dental light guide composed of glass, plastic, or a fiber optic rod containing multiple strands of fibers. The benefit to be realized must be balanced against the fact that for each reflection of light through a tapered conductor, the angle of incidence decreases by an amount equal to twice the taper angle. Thus, if the taper angle is large, the angle of incidence, even for a small number of reflections, will quickly become smaller than the critical angle, at which point light escapes from the light conductor in accordance with Snell's Law of Refraction.

Figure 2:
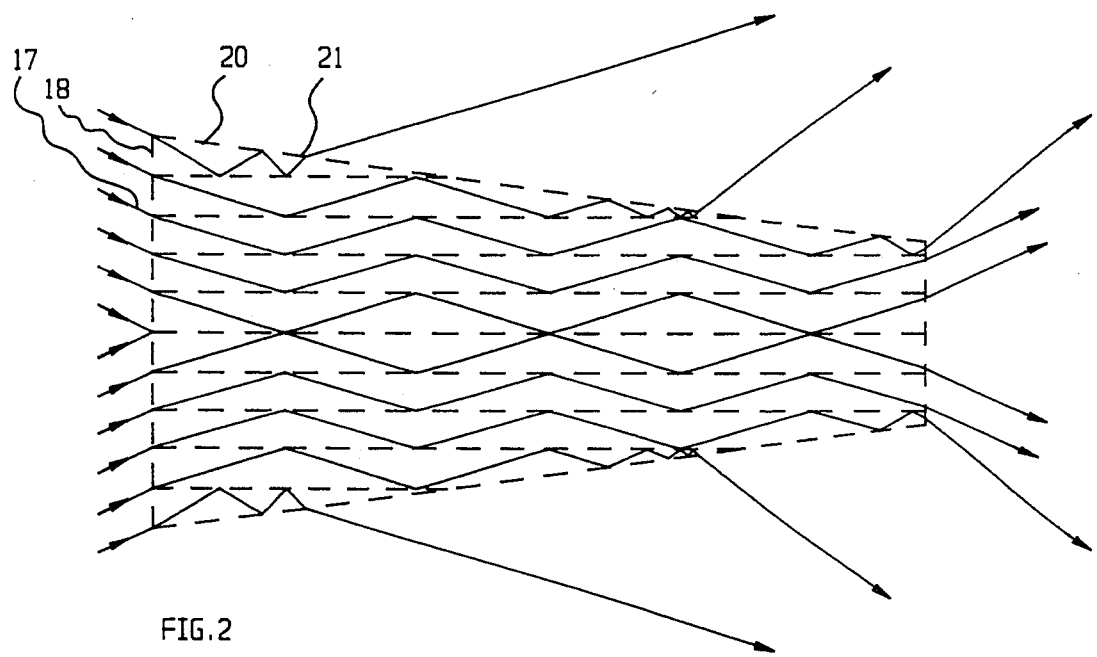
FIG. 2 is a diagrammatic representation showing the effect of parallel light rays through a fiber optic conductor machined to form a conical taper.

If the light conductor is a fiber optic conductor containing multiple fiber strands, and is mechanically contoured to form a conical geometry, the conical surface will permit light to escape through light scattering. This is evident from FIG. 2 showing how parallel light rays (17) incident at the light-receiving surface (18) of a solid, fiber optic light guide (20), which has been machined down to form a conical surface geometry. The parallel light rays (17) scatter out of the light guide (20) along The ground taper (21). Thus, the concept of using a tapered body is rot applicable to a mechanically contoured fiber optic rod. For this reason, the concept of a tapered wave guide has been applied, to date, only to a solid conductor composed of glass or plastic.

Figure 6:
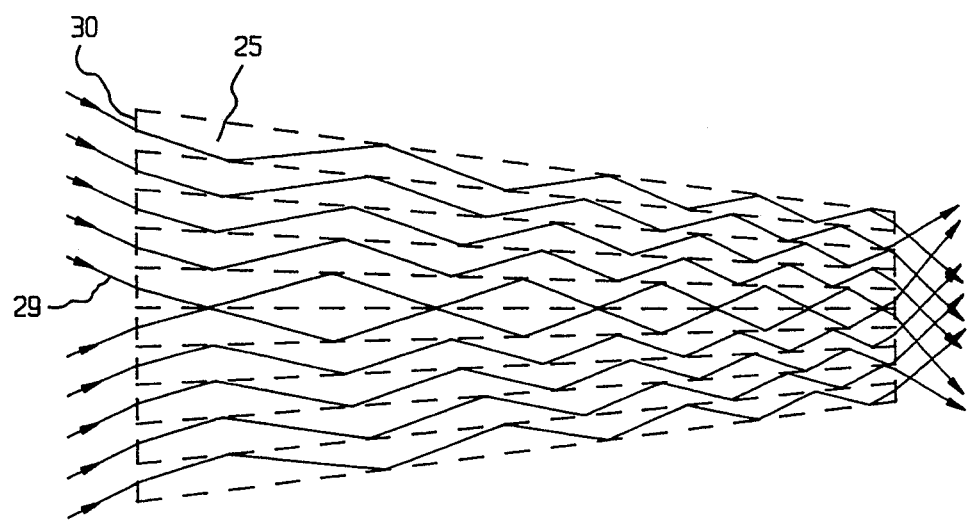
FIG. 6 is a diagrammatic representation showing the effect of parallel fight rays through a fiber optic conductor formed in accordance with the present invention.
Figure 4:
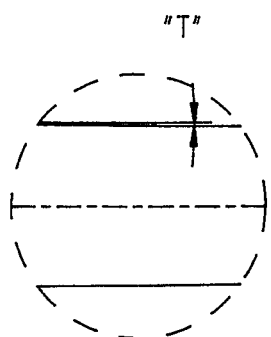
FIG. 4 is a cross-section of the fiber optic conductor of FIG. 3, taken along the lines 4—4 of FIG. 3.
Figure 3:
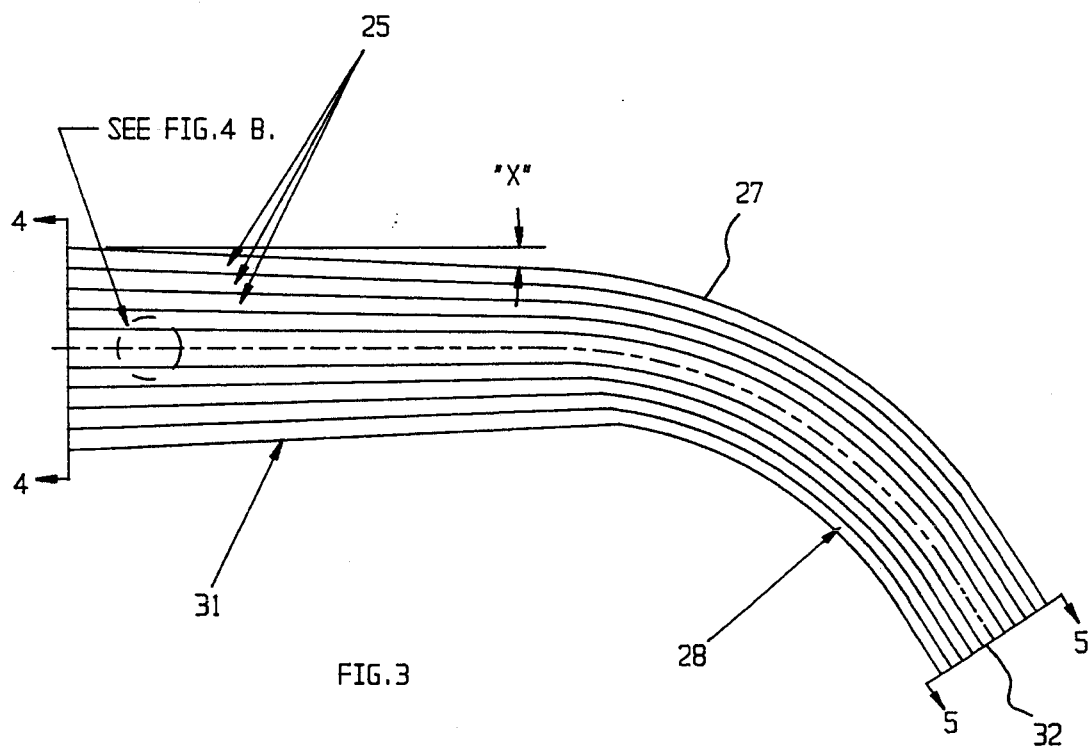
FIG. 3 is a diagrammatic representation of the fiber optic light guide of the present invention, which illustrates the principle of stacking fibers one upon the other to form an optical taper for the bundled conductor, with a taper angle proportional to the number of fibers and the taper angle of each fiber.
Figure 4:
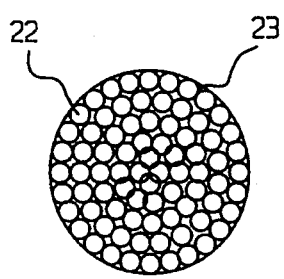
Figure 4:
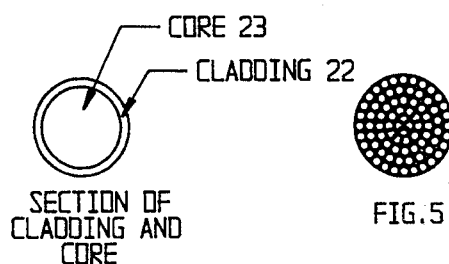
Figure 5:
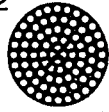
FIG. 5 is a cross-section of the fiber optic conductor of FIG. 3, taken along the lines 5—5 of FIG. 3.

The fiber optic arrangement of the present invention is schematically illustrated in FIGS. 3 through 6. Each fiber strand (25) of the fiber optic conductor (27) is composed of a central core (22) surrounded by a cladding (23), as shown in FIGS. 4 and 4A, to form a composite. In accordance with the present invention, each strand (25) in the conductor (27) has a taper separate from the taper of each other strand (25). To form a conductor (27) having individual tapered strands, each of the fiber optic strands (25) may be separately tapered, bundled and fused together to form a solid conductor (27), or a length of solid fiber optic; may be stretched to form an elongated stretched section of conical geometry wherein each strand is uniformly tapered over the stretched section. The tapered section may then be cut out from the stretched body so that each fiber optic strand (25) is uniformly tapered throughout its length. A curved end section (28) may thereafter be formed by heating and reshaping one end (28). This leaves an elongated, tapered, conical section (31) and a curved end section (28). It is, however, not essential for the curved end section (28) to be tapered, i.e., the curved end section (28) may be of a uniform or more uniform diameter. In either event, the diameter of the fiber optic conductor (27) at its distal end (32), as is shown in FIG. 5, will be substantially reduced in size, based on the taper of the conductor (27) and its length. Although, The diameter of the conductor (27) at the distal end (32) will be substantially smaller than the diameter along the conical section (31), the number of fibers throughout the conductor (27) remains the same. In this arrangement, as shown in FIG. 6, parallel light rays (29) incident at The light-receiving surface (30) are internally reflected through each fiber optic strand (25) without suffering any light scattering. Moreover, as shown in FIGS. 3 and 4B, the taper angle ("T") of each fiber optic strand, measured from the longitudinal axis extending through the center of the light guide, cumulatively creates an optical taper angle ("X") for the light guide in direct proportion to the number of tapered strands in the bundle, multiplied by the taper angle ("T") of each strand.

Thus, if there are, for example, 100 fibers laid side by side across the diameter of a bundle of fiber optic strands, and the optical taper angle for the entire bundle is, e.g., five degrees (5°), then each fiber would be tapered by approximately five/hundreds of a degree (0.05°). This means that each individual fiber has almost the same optical properties of a parallel fiber. Stated otherwise, with only a 0.05 degree taper, it would take a significant number of multiple, internal reflections before the internal angle of incidence is reduced within the individual fiber strand to the critical angle.

The cladding (23) formed around the central core (22) of each fiber optic strand (25), as shown in FIG. 4 and 4A, is of itself conventional and is formed by doping the glass material to controllably reduce the refractive index of the cladding (23). It is necessary for the refractive index of the core (22) to be greater than the refractive index of the cladding. Preferably, the core should have a refractive index of 1.62 and the cladding a refractive index of 1.42.

What is claimed:

1. A fiber optic light guide comprising:
   a multiplicity of fiber optic strands bundled together to form a solid conductor, having an elongated, conical-shaped section and a curved section extending distally from the conical section, with each fiber optic strand composed of a tapered core having a predetermined refractive index, and a cladded coating having a refractive index lower than the refractive index of said core, and with the taper of each fiber optic strand providing a taper angle substantially equivalent to the taper angle of each other fiber optic strand, such that the cumulative taper of all of said fiber optic strands form an optical taper for said conductor, with a taper angle proportional to the number of tapered strands multiplied by the taper angle of said fiber optic strands.

2. A fiber optic light guide, as defined in claim 1, wherein each fiber optic strand in said curved section is tapered.

3. A fiber optic light guide, as defined in claim 2, wherein the taper angle of each fiber optic strand is less than one-tenth of a degree (<0.1°), and the taper angle for said light guide is less than five degrees (<5°).

4. A fiber optic light guide, as defined in claim 3, wherein said curved section has an angle of curvature of from thirty (30°) to sixty degrees (60°) for a diameter range of from 0.3 to 0.6 inches.

5. A light-curing unit for producing a concentrated, high-intensity light, comprising a light source, a reflector for said light source, and a light guide for transmitting reflected light from said light source as a concentrated, high-intensity beam, said light guide having a light-receiving surface transverse to the optic axis of the light source, and a diameter at said light-receiving surface of between 8 mm to 13 ram, with said light guide composed of a multiplicity of fiber optic strands bundled together for forming an elongated conical section and a curved section, with each strand in said conical section having a uniform taper with a taper angle of less than one-tenth of one degree (<0.1°).

6. A light-curing unit, as defined in claim 5, wherein each fiber optic strand has a central core of predetermined refractive index and a cladding of a refractive index lower than the refractive index of the core.

7. A light-curing unit, as defined in claim 6, wherein the cumulative taper angle of said light guide is less than five degrees (<5°).

8. A fiber optic light guide for transmitting a concentrated, high intensity light from a light source to a photocurable dental composition comprising a multiplicity of fiber optic strands bundled together to form a solid conductor and having a conical shaped tapered section and a curved section extending distally from the conical section with the conical section having a taper angle of less than 5 degrees formed by the method of stretching said multiplicity of optical fibers in unison to form said conical shaped tapered section in which each fiber is tapered to a uniform taper angle of less than 1/10 of a degree (<0.1°) and bending said conical section at the distal end thereof to form said curved section.

* * * * *